United States Patent [19]

Byrne et al.

[11] Patent Number: 5,302,604

[45] Date of Patent: Apr. 12, 1994

[54] CHOLESTEROL LOWERING COMPOUNDS PRODUCED BY DIRECTED BIOSYNTHESIS

[75] Inventors: Kevin M. Byrne, West Trenton; Shieh-Shung T. Chen, Morganville, both of N.J.; Louis Kaplan, New City, N.Y.; John G. MacConnell, Westfield, N.J.; Brian R. Petuch, Florence, N.J.; Raymond F. White, Palmyia, Va.; Byron H. Arison, Watchung, N.J.

[73] Assignee: Merck & Co., Inc., Rahway, N.J.

[21] Appl. No.: 957,316

[22] Filed: Oct. 6, 1992

Related U.S. Application Data

[63] Continuation-in-part of Ser. No. 848,628, Mar. 9, 1992, abandoned.

[51] Int. Cl.$^5$ .................... A61K 31/38; A61K 31/44; C07D 493/08
[52] U.S. Cl. .................... 514/338; 514/397; 514/444; 514/452; 514/414; 546/270; 548/311.7; 548/463; 549/60; 549/363
[58] Field of Search .................. 549/60, 363; 546/270; 514/444, 452, 338, 397, 414; 548/311.7, 463

[56] References Cited

U.S. PATENT DOCUMENTS 5,019,390  5/1991  McCarthy et al. .................... 514/2
5,053,425  10/1991 Bartizal et al. .................... 514/452
5,096,923  3/1992  Bergstrom et al. .................. 514/452

FOREIGN PATENT DOCUMENTS 0494622  7/1992  European Pat. Off. .
0503520  9/1992  European Pat. Off. .
WO93/07151  4/1993  PCT Int'l Appl. .
WO92/12156  7/1992  World Int. Prop. O. .
WO92/12157  7/1992  World Int. Prop. O. .
WO92/12158  7/1992  World Int. Prop. O. .
WO92/12159  7/1992  World Int. Prop. O. .
WO92/12160  7/1992  World Int. Prop. O. .

OTHER PUBLICATIONS

Kobel and Traber, European Journal App. Microbiol. Biotechnol. 14: 237–240 (1982).
Hensens et al., J. Antibiotics, 45: 133–135 (1992).

Primary Examiner—Richard L. Raymond
Attorney, Agent, or Firm—Catherine A. Dolan; Melvin Winokur; Paul D. Matukaitis

[57] ABSTRACT

Compounds of Structural Formula (I)

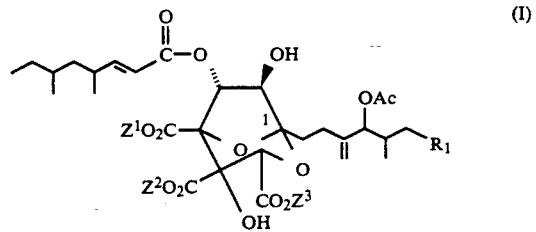

are produced by directed biosynthesis. These compounds are squalene synthetase inhibitors and thus useful as cholesterol lowering agents, antifungal agents and cancer treatment agents.

17 Claims, No Drawings

CHOLESTEROL LOWERING COMPOUNDS PRODUCED BY DIRECTED BIOSYNTHESIS

CROSS REFERENCE TO RELATED APPLICATIONS

This application is a continuation-in-part of U.S. application Ser. No. 07/848,628, filed Mar. 9, 1992, now abandoned.

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOR® (lovastatin), now commercially available, is one of a group of very active antihypercholesterolemic agents that function by limiting cholesterol biosynthesis by inhibiting the enzyme, HMG-CoA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E.J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorus containing inhibitors of squalene synthetase have been isolated as natural products. These natural product inhibitors are described in U.S. Pat. Nos. 5,053,425; 5,055,487 and 5,026,554.

U.S. Pat. No. 5,053,425 discloses a zaragozic acid compound of structure

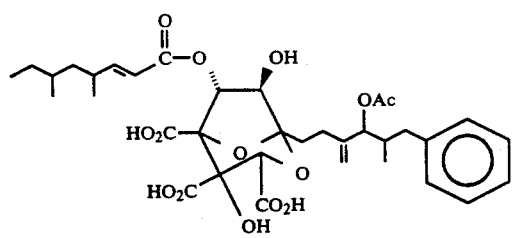

hereafter referred to as zaragozic acid A. Applicants have now found that providing certain aryl, heteroaryl, aralkyl or heteroaralkyl carboxylic acids to a culture that produces zaragozic acid A leads to the incorporation of an aryl or heteroaryl moiety into the C-1 side chain of zaragozic acid A.

DETAILED DESCRIPTION OF THE INVENTION

The present invention is directed to compounds of structural formula (I):

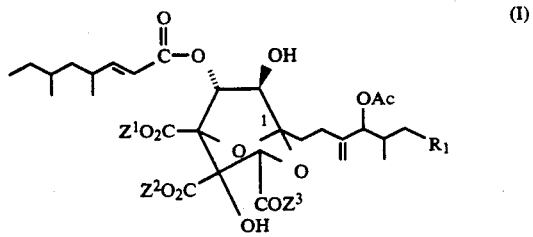

wherein $R_1$ is selected from

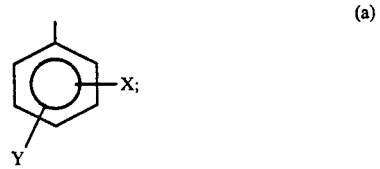

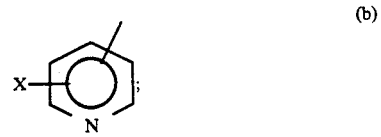

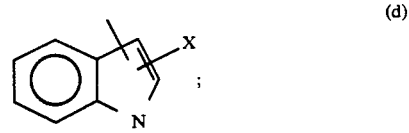

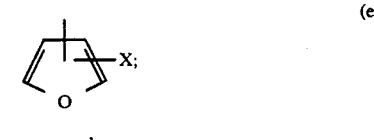

and

wherein X and Y are selected from the group consisting of:
  (a) H;
  (b) halogen (F, Cl, Br, I);
  (c) OH; and
  (d) $CH_3$, provided that when $R_1$ is phenyl, X and Y are not both hydrogen;
and wherein $Z^1$, $Z^2$ and $Z^3$ are each independently selected from the group consisting of
  (a) H;
  (b) $C_{1-5}$alkyl;
  (c) $C_{1-5}$alkyl substituted with a substitutent selected from the group consisting of:
    (i) phenyl, and (ii) phenyl substituted with methyl, methoxy, halogen (Cl, Br, I, F) or hydroxy; and
(iii) $C_{1-5}$alkylcarbonyloxy;
(iv) $C_{6-10}$arylcarbonyloxy;
(v) $C_{1-5}$alkoxycarbonyloxy;
(vi) $C_{6-10}$aryloxycarbonyloxy;
(vii)

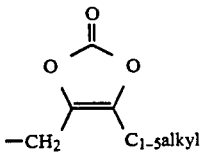

(viii)

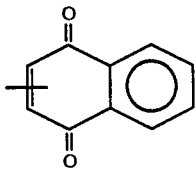

(ix) or the groups (iii) to (vi) form a 5 to 10 membered mono or bicyclic ring with C1-5alkyl; and a pharmaceutically acceptable salt thereof; pharmaceutical compositions thereof, and their use as squalene synthetase inhibitors and their use as cholesterol lowering agents, antifungal agents and cancer treatment agents.

In one class of this embodiment $R_1$ is selected from

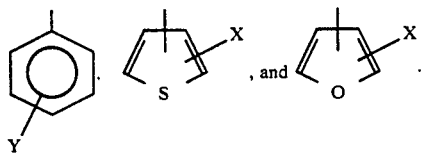

Exemplifying this class are the compounds wherein X is selected from H and F; and Y is F.

The compounds of the present invention are formed in a directed biosynthesis which comprises the addition of a compound of Formula (II) selected from the group consisting of:

(a) $R_1$—$CO_2H$; and
(b) $R_1$—$CH_2$—$CHNH_2CO_2H$;

wherein $R_1$ is as defined above, to a zaragozic acid A producing culture and isolating the product (I) from the culture broth.

Known zaragozic acid A producing cultures suitable for producing the compounds of the present invention include:

(a) MF5453 (ATCC 20986),
(b) MF5565 (ATCC 74068),
(c) MF5599 (ATCC 74065),
(d) MF5572 (ATCC 74066),
(e) MF5573 (ATCC 74067).

The culture MF5453 is that of a fungus isolated from a water sample obtained from the Jalon River, Zaragoza, Spain. This culture has been deposited with the American Type Culture Collection at 12301 Parklawn Drive, Rockville, Md. 20852 as ATCC 20986. The microorganism MF5453, its morphological characteristics and a fermentation procedure using this microorganism have been described in U.S. Pat. No. 5,053,425.

The culture MF5565 is a strain of *Exserohilum rostratum*, which was isolated from bark of *Theobroma cacao* (Philippines). The culture has been deposited with the ATCC as ATCC 74068. The microorganism MF5565, its morphological characteristics and a fermentation procedure using this microorganism have been described in U.S. Pat. application Ser. No. 722,049 filed Jun. 27, 1991.

This strain, MF5565, was recovered from the bark of *Theobroma cacao*, collected in Los Banos, Laguna Province, Philippines. Bark discs were removed with a leather punch (no. 245, C. S. Osborne & Co., Harrison, N.J.). Discs were approximately 1 cm in diameter and 0.3-1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar medium (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to one month for the development of fungal colonies on bark discs and the gear.

Strain MF5565 exhibits the following morphological characteristics.

Colonies relatively fast-growing, in 1 week attaining a diameter of: 50 mm on cornmeal agar (Difco Laboratories); 50-52 mm on yeast-malt extract agar (10 g malt extract, 2 g yeast extract, 20 g agar in 1 L distilled water); 60 mm on V8 juice agar (200 mL V8 juice, Campbell Soup Co., 3 g $CaCO_3$, 20 g agar diluted to 1 L distilled water). On yeast-malt agar with both submerged and aerial mucelium, with submerged mycelium sometimes forming radial strands, floccose to cottony or lanose in age, with margin appressed, minutely fimbriate to even, hyaline to pale gray at the margin but soom darkening to dark gray or dark olive-gray, or black in age, Dark Olive-Gray, Iron Gray, Dark Mouse Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions. Odors, sclerotia, stromata, or pseudothecia absent. Conidiophores arising from uppermost aerial mycelium, up to 600 μm long, 3-4.5 μm wide, straight or flexuous, with geniculate apices, with walls smooth, or occasionally finely incrusted, usually bearing 2-10 conidia, pale olive-gray to olive-gray. Conidiogenous cells polytretic, integrated, sympodial, indeterminate, terminal or intercalary, with slightly raised, darkened scars surrounding a minute pore at the conidiogenous locus. Conidia 45-250×7-20 μm, mostly 75-180 μm long, variable in shape, broadly ellipsoidal, fusoid, obclavate, or tapered cylindrical, straight to curved, or rarely sigmoid, with broadly rounded apices, smooth, 5-22 septate, with basal septum most thickened and darkened, with terminal septum often also darker than septa delimiting central cells, with a distinct cylindrical hilar appendix protruding 1–2.5 μm, pedicel-like extensions absent, initially germinating from apical and basal cells pale gray to olive-gray in 3% KOH. Hyphae septate, branched, pale olive-gray to olive-brown, usually smooth, but occasionally with fine incrustations.

Strain MF5565 belongs to the genus *Exserohilum rostratum* based on the combination of polytretic conidiogenous cells that give rise to predominately multiseptate, dematiaceous phragmoconidia. The basal cell of the conidium is delimited by a thick, darkened septum, and has a protruding hilar appendix. Strain MF5565 is identified as *Exserohilum rostratum* based on the predominance of straight and curved conidia, darkened septa delimiting both the basal and terminal cells, and relatively long conidia (A. Sivanesan. 1987 Graminicolous species of Bipolaris, Curvularia, Drechslera, Exserohilum and their telemorphs. CMI Mycological Paper No. 158).

The culture MF5599, is a strain of *Curvularia lunata* var. aeria isolated from bark of *Ficus elastica* (Diliman, Quezon City, Philippines). The culture has been deposited with the ATCC as ATCC 74065. The microorganism MF5599 has the same morphological characteristics as MF5572, described below.

The culture MF5572 is a strain of Curvularia lunata var. aeria, isolated from tree bark (Philippines). This culture has been deposited with the ATCC as ATCC 74066. The microorganism MF5572, its morphological characteristics and a fermentation procedure using this microorganism have been described in U.S. patent application Ser. No. 715,535 filed Jun. 14, 1991.

Strain MF5572, was recovered from the bark of an unidentified tree, collected in Diliman, Quezon City, Philippines. Bark discs were removed with a leather punch (no. 245, C. S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5572 has been identified as *Curvularia lunata* var. aeria and exhibits the following morphological characteristics.

Colonies are relatively fast-growing, in 1 week attaining a diameter of: 30–35 mm on cornmeal agar (Difco Laboratories); 30–35 mm on yeast-malt extract agar (10 g malt extract, 2 g yeast extract, 20 g agar in 1 L distilled water); 40–55 mm on V8 juice agar (200 mL V8 juice, Campbell Soup Co., 3 g $CaCO_3$, 20 g agar diluted to 1 L distilled water). On yeast-malt agar both submerged and aerial mycelia form, are slightly raised in side view, velvety to floccose when young, cottony or lanose in age, with margin slightly raised, even to wavy, hyaline to pale gray at the margin but soon darkening to grayish olive, gray, to dark olive-gray, Smoke Gray, Light Grayish Olive, Deep Olive-Gray, Dark Olive-Gray, Iron Gray, Castor Gray (capitalized color names from Ridgway, R. 1912. Color Standards and Nomenclature, Washington, D.C.), in reverse yellowish gray towards the margin but soon olivaceous gray, in age developing dark olive-black spots and patches in the agar, often with patches or tufts of hyaline to pale gray aerial hyphae developing in older portions, odors and pseudothecia absent. The surface of cultures in excess of 3 weeks old, generally develop straight to curved, cylindrical, finger-like stromata, 0.5–1 mm tall, which project upward from the oldest regions of the colony surface. Stromata formation is best on nutrient-rich media, e.g. potato-dextrose agar, oatmeal agar, or glucose-yeast-malt extract agar.

Conidiophores arising from aerial hyphae, 30–200×3–5 μm, septate, straight or flexuous, sometimes branched in age, with apices straight, curved or geniculate, smooth, thin-to slightly thick-walled, olive-brown to olive-gray in 3% KOH, bearing 2–10 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 18–28×9–14 μm, consistently 3-septate, broadly elliptical, with penultimate, distal cell curved and distinctly swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched. Stromatic tissue a textura intricata, with cells hyaline in 3% KOH.

The culture MF5573, *Curvularia lunata* var. lunata, was isolated from *Ficus elastica* tree bark (Philippines). The culture has been deposited with the ATCC as ATCC 74067. The microoganism MF5573, its morphological characteristics and a fermentation procedure using this microorganism have been described in U.S. patent application Ser. No. 715,535 filed Jun. 14, 1991.

*Curvularia lunata* var. lunata MF5573 was recovered from the bark of *Ficus elastica* collected in Diliman, Quezon City, Philippines. Bark discs were removed with a leather punch (no. 245, C.S. Osborne & Co., Harrison, N.J.). Discs were approximately 1 cm in diameter and 0.3–1.0 cm thick depending on the thickness of the bark and amount of force used to hammer the punch into the tree. Discs included an entire bark cross-section along with the vascular cambium, and sometimes a veneer of the outer xylem. Discs from each tree were placed in manila coin envelopes for transport to the laboratory. Discs were soaked in 10% household bleach for 3 minutes, rinsed with sterile distilled water and briefly flamed with an alcohol lamp prior to application to isolation media. Bark discs were applied outer side down to an agar media (10 g malt extract, 2 g yeast extract, 1 g sodium propionate, 5 g dehydrated bovine bile, 1 mg benomyl, 50 mg streptomycin sulfate, 50 mg chlorotetracycline, 20 g agar in 1 L distilled water) in 100 mm diameter plastic Petri dishes. Petri dishes were incubated at 24° C., and inspected more or less daily for up to two weeks for the development of fungal colonies on bark discs and the agar.

Strain MF5573 has been identified as *Curvularia lunata* var. lunata and exhibits the following morphological characteristics.

Colonies are relatively fast-growing, in 1 week attaining a diameter of: 35–40 mm on cornmeal agar (Difco Laboratories); 40 mm on yeast-malt extract agar (10 g malt extract, 2 g yeast extract, 20 g agar in 1 L distilled water); 45–50 mm on V8 juice agar (200 mL V8 juice, Campbell Soup Co., 3 g CaCO₃, 20 g agar diluted to 1 L distilled water). On yeast-malt agar both submerged and aerial mycelia form, with aerial mycelia sometimes forming radial strands, floccose to cottony or lanose in age, with margin appressed, minutely fimbriate, hyaline to pale gray at the margin but soon darkening to dark gray or dark olive-gray, Castor Gray, Dark Olive-Gray, Iron Gray, Dusky Green-Gray, Blackish Green-Gray, Olivaceous Black (capitalized color names from Ridgway, R. 1912. Color Standards and Nomenclature, Washington, D.C.), similar in reverse, often with patches or tufts of hyaline to pale gray aerial hyphae developing in older portions, occasionally forming pale gray to hyaline sectors, odors, sclerotia, stromata, or pseudothecia absent.

Conidiophores arising from surface or aerial hyphae, 15–250×3–5 μm, septate, straight or flexuous, sometimes branched in age, with apices straight, curved or geniculate, smooth, thin- to slightly thick-walled, olive-brown to olive-gray in 3% KOH, bearing 4–15 conidia. Conidiogenous cells polytretic, integrated, indeterminate, sympodial, usually terminal on the conidiophore, sometimes intercalary in age, with slightly darkened scars surrounding a minute pore at the conidiogenous locus. Conidia 21–30×9–13.5 μm, usually 3-septate, infrequently 4-septate, broadly elliptical, with penultimate, distal cell curved and often obliquely swollen, with slightly flattened scar at base, without hilar appendix, smooth, pale olive-brown to olive-gray, usually with two central cells slightly darker. Hyphae pale olive-gray to dark olive-gray or olive-brown in 3% KOH, septate, branched.

Vegetative cells of a culture capable of producing zaragozic acids, such as: MF5453 (ATCC 20986); MF5565 (ATCC 74068); MF5599 (ATCC 74065); MF5572 (ATCC 74066); or MF5573 (ATCC 74067) can be obtained by culturing the microorganism in an aqueous nutrient medium containing sources of assimilable carbon and nitrogen, preferably under aerobic conditions. Nutrient media may also optionally contain mineral salts, high molecular weight polyanions (CARBOPOL ®, JUNLON ®), and/or defoaming agents.

The preferred sources of carbon in the nutrient medium are carbohydrates such as glucose, glycerin, and the like. Other sources which may be included are maltose, fructose, sucrose, and the like. In addition, complex nutrient sources such as oat flour, may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, and the like, as well as complex sources such as yeast extracts (hydrolysates, autolysates), dried yeast, tomato paste, peptone, corn steep liquor, malt extracts and the like. Inorganic nitrogen sources such as ammonium salts (e.g. ammonium nitrate, ammonium sulfate, ammonium phosphate, etc.) can also be used. The various sources of nitrogen can be used alone or in combination in amounts ranging between 0.2 to 20 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salt and the like. Also included are trace metals such as manganese, iron, molybdenum, zinc, and the like.

The preferred process for production of these vegetative cells consists of inoculating spores or mycelia of the producing organism into a suitable medium and then cultivating under aerobic condition. After inoculation, the flasks are incubated with agitation at temperature ranging from 20° to 30° C., preferably 24° to 27° C. Agitation rates may range up to 400 rpm, preferably 200 to 240 rpm. Flasks are incubated over a period of 2 to 10 days, preferably 2 to 4 days. When growth is plentiful, the culture is ready to be washed, homogenized, and used in directed biosynthetic studies.

In addition, the compounds of the present invention may be more selectively synthesized by inhibiting the enzyme phenylalanine ammonia lyase (PAL) which is the first step in the degradation of L-phenylalanine to form benzoic acid. Benzoic acid has been shown to be the direct precursor of the aromatic ring system on the C-1 side chain of zaragozic acid A. Inhibitors of PAL include phenylpropiolic acid, D-phenylalanine, aminooxyacetic acid, p-coumaric acid, caffeic acid, D,L-β-phenylserine and D,L-2-hydroxyphenylalanine.

Furthermore, the process of the present invention may be carried out using a mutant for the parent strain that is lacking the PAL enzyme, resulting in a culture whose synthesis of the zaragoic acid A is dependent on an exogenous source of benzoic acid. This culture more readily incorporates the compounds of Formula (II)

$$R_1-CO_2H;$$

because these compounds are not competing with an endogenous source of benzoic acid.

After growth, cells are harvested by filtration or centrifugation. To obtain a uniform suspension, the cell mixture may optionally be homogenized using a homogenizer such as a hand-held BIOHOMOGENIZER ™ (Bartlesville, Okla.) until no clumps or mycelial balls are visible (about 20 to 60 seconds).

Alternatively, the vegetative cells may be grown in media containing polyanions to give more beaded and grainy growth, which may eliminate the benefits of the homogenization step which transforms large balled growth to more disperse hyphal fragments.

After growth or the optional homogenization step, the cells are harvested by filtration or centrifugation, and washed with distilled water or an aqueous buffer and resuspended in a medium consisting of 1 to 5% of a carbon/energy source such as glucose, glycerol, sucrose or the like and an appropriate buffer such as 5–10 mM PIPES (piperazine-N,N'-bis[2-ethanesulfonic acid]), MOPS (3-[N-morpholino]propanesulfonic acid), MES (2-[N-morpholino]ethanesulfonic acid), MOPSO (3-[N-morpholino]-2-hydroxypropanesulfonic acid), ACES (N-[2-acetamido]-2-aminoethanesulfonic acid), ADA (N-[2-acetamido]-2-iminodiacetic acid), BES (N,N-bis[2-hydroxyethyl]-2-aminoethanesulfonic acid), phosphate or the like to keep the pH less than 8, preferably pH 6 to pH 6.5. In order to guarantee uniform suspension of the cells, the container holding the cells is shaken vigorously.

Aliquots of the suspended cells are removed and are incubated at 20° to 30° C. for 24 to 144 hours with or without agitation, preferably at 25° C. for 120 hours with agitation. After this initial incubation, a compound of Formula (II), selected from $R_1$—$CO_2H$ and $R_1$—$CH_2$—$CHNH_2CO_2H$ wherein $R_1$ is as noted above on pages 3 to 4, is added, either as a free acid or as a biologically acceptable salt form such as sodium to a final concentration of 0.01 mM to 100 mM, preferably 0.25 to 0.5 mM, followed by additional incubation of 48 to 120 hours. After the additional incubation, the biosynthesis is terminated by the addition of a solvent such as methanol or acetonitrile, preferably methanol, and the broth is clarified.

In order to make the cells more permeable to the uptake of the compounds of Formula (II), the cells may be treated with toluene vapors by adding 1-2 drops of toluene to the aliquot of cells after the initial incubation. The suspension is vigorously shaken at ambient temperature for 30 seconds, followed by the addition of a compound of Formula (II) to the suspension of cells and the additional incubation as described above.

The desired compounds of Formula (I) are extracted with solvent and purified by various chromatographic techniques such as silica gel, reverse phase and ion exchange. Preferably the compounds of Formula (I) are isolated by anion exchange chromatography followed by preparative reverse-phase high pressure liquid chromatography.

Esters of the compound of Formula (I) may be prepared by dissolving the compound of Formula (I) in a dry organic solvent, preferably tetrahydrofuran (THF) at 0°-30° C. and treating with the appropriately substituted isourea for 8-24 hours, cooling to $-15°$ C. and filtering the urea. The mono-, di- and tri-esters may be prepared by varying the number of equivalents of isourea used. The filtrate is concentrated under reduced pressure to yield the desired ester. Esters may also be prepared by treating a compound of formula (I) with an organic halide (chloride, bromide or iodide) in a standard organic solvent in the presence of a base such as triethylamine, pyridine or DBU. Mono, di and triesters may be formed by using the appropriate number of equivalents of alkylating agent. Mixtures may be separated by HPLC.

The present invention is also directed to a method of inhibiting cholesterol biosynthesis which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemic and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

In addition, the present invention is directed to a method of inhibiting the enzyme squalene synthetase which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)aminomethane, and tetramethylammonium hydroxide. The salts included herein encompass those wherein one, two or all three of the carboxyl groups are in the salt form. These salts may be prepared by standard procedures.

The compounds of this invention may also be administered in combination with other cholesterol-lowering agents such as those which inhibit another enzyme in the biosynthetic pathway in the synthesis of cholesterol. Examples of such agents would include but are not limited to HMG-CoA reductase inhibitors, HMG-CoA synthase inhibitors, and squalene epoxidase inhibitors. Illustrative of such inhibitors are lovastatin, simvastatin, pravastatin and fluvastatin. Other cholesterol lowering agents that may be administered include niacin, probucol, the fibric acids: clofibrate and gemfibrozil, and LDL-receptor gene inducers. Representative of such combinations are those containing about 10-400 mg of a compound of formula (I) in combination with about 20-100 mg of an HMG-CoA reductase inhibitor or 250-1000 mg of probucol or 600-1200 mg of gemfibrozil or 1-2 g of clofibrate, or 3-6 g of niacin, or 20-300 mg of an LDL-receptor gene inducer.

The compounds of this invention may also be co-administered with pharmaceutically acceptable nontoxic cationic polymers capable of binding bile acids in a non-resorbable form in the gastrointestinal tract. Examples of such polymers include cholestyramine, colestipol and poly[methyl-(3-trimethyl)aminopropyl]iminotrimethylene dihalide. The relative amounts for co-administration of the compounds of this invention and these polymers is between 1:100 and 1:15,000 (w/w).

The intrinsic squalene synthetase inhibitory activity of representative compounds of this invention was measured by the standard in vitro protocol described below:

PREPARATION OF RAT LIVER MICROSOMES

Male, Charles River CD rats (120 to 150 g) were fed a diet containing 0.1% lovastatin for 4 days. The livers from these rats were homogenized in 5 volumes (mL/g) of ice cold 50 mM HEPES (4-(2-hydroxyethyl)-1-piperazine-ethanesulfonic acid), 5 mM EDTA (ethylenediaminetetraacetic acid) pH 7.5 with a Potter-Elvehjem type tissue grinder. The homogenate was centrifuged twice at 20,000×g for 15 min. at 4° C., discarding the pellet each time. The supernatant was then centrifuged at 100,000×g for 1 hr at 4° C. The resulting microsomal pellet was resuspended in a volume of the above homogenizing buffer equal to one-fifth the volume of the original homogenate. This microsomal preparation has a protein concentration of about 7 mg/mL. The microsomal suspensions were stored in aliquots at −70° C. Squalene synthetase activity in these aliquots is stable for a least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125–129 (1985)) and a unit of activity is defined as the amount of enzyme that will produce 1 μ mole of farnesyl pyrophosphate per minute at 30° C. in the standard assay.

The livers of 23 forty-day old male rats that had been fed 5% cholestyramine plus 0.1% lovastatin were homogenized in a WARING ™ blender in 1 liter of 10 mM mercaptoethanol, 2 mM EDTA, 25 mM leupeptin, 0.005% phenylmethylsulfonyl fluoride, pH 7.0 containing 0.1 trypsin inhibitor units of aprotinin/mL. The homogenate was centrifuged at 20,000× g for 20 min. The supernatant was adjusted to pH 5.5. with 6N HOAc and centrifuged at 100,000× g for 1 hour. This supernatant was adjusted to pH 7.0 with 3N KOH and a 35–60% ammonium sulfate fraction was taken. The 60% pellet was redissolved in 60 mL of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5×5 cm column of DEAE-sepharose 4B equilibrated with Buffer A. The column was washed with 700 mL of Buffer A and a 1 liter gradient from Buffer A to 100 mM potassium phosphate, 10 mM mercaptoethanol, 1 mM EDTA, pH 7.0. Fractions having a specific activity greater than 0.20 units/mg were combined, solid ammonium sulfate was added to bring to 60% saturation and pelleted. The pellet was dissolved in 8 mL of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/mL with specific activity of 0.23 units/mg and was free of isopentenyl pyrophosphate isomerase activity. This ammonium sulfate suspension was used for the synthesis of [4-$^{14}$C]farnesyl-pyrophosphate and its activity was stable stored at 4° C. for a least 6 months.

ENZYMATIC SYNTHESIS OF [4-$^{14}$C]FARNESYL-PYROPHOSPHATE

The solvent (ethanol: 0.15N NH$_4$OH, 1:1) was removed from 55 mCi of [4-$^{14}$C]isopentenyl pyrophosphate (47.9 mCi/mmole) by rotary evaporation. Six hundred microliters of 100 mM Tris, 10 mM MgCl$_2$, 4 mM dithiothreitol pH 7.5 was added and the solution was transferred to a 1.5 mL Eppendorf centrifuge tube. Geranyl-pyrophosphate, 250 microliters of a 20 mM solution, and 50 microliters of the ammonium sulfate suspension of prenyl transferase were added to initiate the reaction. This incubation contained 5 micromoles of geranyl pyrophosphate, 1.15 micromoles of isopentenyl pyrophosphate, 6 micromoles of MgCl$_2$ and 0.18 units of prenyl transferase in a volume of 900 microliters. The incubation was conducted at 37° C. During the incubation, the mix turned cloudy white as the newly formed magnesium complex of farnesyl pyrophosphate precipitated out of solution. The [4-$^{14}$C]farnesyl pyrophosphate was collected by centrifugation for 3 minutes at 14,000 rpm in an Eppendorf centrifuge tube, the supernatant removed, and the pellet was dissolved in 1.0 mL of 50 mM HEPES, 5 mM EDTA, pH 7.5. The yield was 50.7 μCi (92%) of [4-$^{14}$C]farnesyl pyrophosphate. The [4-$^{14}$C]farnesyl pyrophosphate was stored in aliquots at −70° C.

SQUALENE SYNTHETASE ASSAY

Reactions were performed in 16×125 mm screw cap test tubes. A batch assay mix was prepared from the following solution:

| | mL per assay | volume for 50 assays |
|---|---|---|
| 1. 250 mM HEPES pH 7.5 | 20 | 1000 |
| 2. NaF 110 mM | 10 | 500 |
| 3. MgCl$_2$ 55 mM | 10 | 500 |
| 4. Dithiothreitol 30 mM | 10 | 500 |
| 5. NADPH 10 mM (made fresh) | 10 | 500 |
| 6. [4-$^{14}$C]farnesyl-pyrophosphate 47.9 μCi/μmole, and 0.025 μCi/3.0 μL | 3.0 | 150 |
| 7. H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 μL of the assay mix was taken with 3 μmL of an inhibitor solution (DMSO or MeOH in the controls), warmed to 30° C. in a water bath and then the reaction was initiated by the addition of 10 mL of the 1:120 dilution of microsomal protein (0.6 μg protein total in the assay). The reactions were stopped after 20 minutes by the addition of 100 μL of a 1:1 mix of 40% KOH with 95% EtOH. The stopped mix was heated at 65° C. for 30 min., and cooled. Ten mL of heptane was added and the mix was vortexed. Two g of activated alumina was then added, the mix vortexed again, the alumina allowed to settle and 5 mL of the heptane layer was removed. Ten mL of scintillation fluid was added to the heptane solution and radioactivity was determined by liquid scintillation counting.

Percent inhibition is calculated by the formula:

$$1 - \frac{[\text{Sample} - \text{Blank}]}{[\text{Control} - \text{Blank}]} \times 100$$

Representative of the activity of the compounds of the present invention is that below:

| Compound | Squalene Synthetase IC$_{50}$ |
|---|---|
| Formula (I) wherein Z$^1$, Z$^2$, and Z$^3$ are each hydrogen and | 0.14 ng/mL |

| Compound | Squalene Synthetase IC$_{50}$ |
|---|---|
| R$_1$ is 3-thiophene | |

The present compounds also demonstrate broad spectrum antifungal activity. Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

Furthermore, the compounds of the present invention inhibit farnesyl-protein transferase and thereby inhibit the farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (FTase) from bovine brain is chromatographed on DEAE-Sephacel (Pharmacia, 0–0.8M NaCl gradient elution), N-octyl agarose (SIGMA ®, 0–0.6M NaCl gradient elution), and a MONO Q ® HPLC column (Pharmacia, 0–0.3M NaCl gradient). Ras-CVLS at 3.5 μM, 0.25 μM [$^3$H]FPP, and the indicated compounds are incubated with this partially purified enzyme preparation.

RASIT ASSAY II

Farnesyl-protein transferase (FTase) from bovine brain was chromatographed on DEAE-Sephacel (Pharmacia, 0–0.8M NaCl gradient elution), N-octyl agarose (SIGMA ® 0–0.6M NaCl gradient elution), and a MONO O ® HPLC column (Pharmacia, 0–0.3M NaCl gradient). Ras-CVLS at 1.0 μM, 0.5 μM [$^3$H]FPP, and the indicated compounds are incubated with this partially purified enzyme preparation. The FTase data is a measurement of the ability of the test compound to inhibit Ras farnesylation in vitro.

The pharmaceutical compositions containing the compounds of structural Formula (I) inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably between 0.5 mg/kg of body weight to about 10 mg/kg of body weight of a mammal a day.

The following examples illustrate the formation of a compound of formula (I).

EXAMPLE 1

A Compound of Formula (I) wherein R$_1$ is 3-thiophene and Z$^1$, Z$^2$ and Z$^3$ are each hydrogen I. Directed Biosynthesis:

Culture MF5453 was grown for 72 hours at 25° C. in KF medium (U.S. Pat. No. 5,053,425) and the cells harvested by centrifugation. The cells were washed (X2) with distilled water and resuspended to the original broth volume in 20 mM piperazine-N,N'-bis[2-ethanesulfonic acid] (PIPES) buffer (pH 6.1) containing 3% sucrose. Five mL aliquots of this suspension were transferred to each of four 50 mL Erlenmeyer flasks and these flasks incubated at 25° C. with agitation. After 24 hours incubation, 3-thiophene-carboxylic acid (Na-salt) was added to a final concentration of 0.25 mM, 0.5 mM and 1.0 mM to each of three of the flasks respectively, and the fourth remained a control. After an additional 96 hours incubation the biosynthesis was terminated with the addition of two volumes of methanol and the broths clarified. The broth-methanol mixture was adjusted to pH 4.5 with formic acid. The contents of the three flasks to which the 3-thiophene carboxylic acid had been added were combined. The resulting mixture was applied to a 1 mL column of BIO-RAD ® AG4X4 ion exchange resin in the formate cycle. The column was washed successively with 15 mL of MeOH-formate buffer (1/1 v/v; 50 mM formate adjusted to pH 4.5) and 15 mL of 60/40 MeCN/water (v/v). The column was then eluted with 15 mL of 60/40 MeCN/water containing 1 mL concentrated formic acid.

II. Isolation and Purification:

Fifteen mL of AG4X4 eluate was reduced under nitrogen to 8 mL. The crude extract was filtered and 2 mL injected onto a BECKMAN ® preparative HPLC (9.6 mm×250 mm) ODS column. The column was developed at 3.0 mL/min using a 35 minute linear gradient of 40% to 80% acetonitrile in water containing 0.1% H$_3$PO$_4$. Detection was at 215 nm. Peaks with an elution time of 28.9 minutes were collected and pooled. The pooled material was diluted with four volumes of deionized water and applied to a water-equilibrated C$_{18}$ SPE column. After washing with five volumes of deionized water, the column was dried with nitrogen, then eluted with methanol. The eluate was evaporated to dryness to yield a substance identified as the title compound.

$^1$H NMR (400 MHz) (CD$_3$OD) 7.29 (dd, J=4.9, 30, 1H), 7.03 (dd, 2.9, 1.4, 1H), 6.98 (dd, 4.9, 1.4, 1H), 6.86 (dd, 15.7, 8.4, 1H), 6.43 (d, 2.1, 1H), 5.83 (dd, 15.7, 1.0,

1H), 5.11 (d, 5, 1H), 5.07 (s, 1H), 5.02 (s, 1H), 4.94 (s, 1H), 4.04 (d, 2.1, 1H), 2.69 (dd, 14, 6, 1H), 2.49 (dd, 14, 8.7, 1H), 2.42 (m, 1H), 2.26 (m, 2H), 2.08 (s, 3H), 2.05 (m, 1H), 1.26–1.41 (m, approximately 3H), 1.15 (m, 2H), 1.02 (d, 6.5, 3H), 0.86 (d, ca 6.5, 3H), 0.85 (t, ca 7, 3H), 0.84 (d, ca 6.5, 3H).

EXAMPLE 2

Compound of Formula (I) wherein $R_1$ is 3-fluorophenyl and $Z^1$, $Z^2$ and $Z^3$ are each hydrogen

I. DIRECTED BIOSYNTHESIS:

Culture MF 5453 was grown for 72 hours at 25° C. in KF medium and the cells harvested by centrifugation. The cells were washed twice with distilled water and resuspended to the original broth volume in 20 mM PIPES buffer (pH 6.1) containing 3% sucrose. Five mL aliquots of this suspension were transferred to 50 mL Erlenmeyer flasks and these flasks incubated at 25° C. with agitation. After 24 hours' incubation, 3-fluorobenzoic acid (Na-salt) was added to a final concentration of 0.25 mM. After 24 hours incubation, additional 3-fluorobenzoic acid was added to a final concentration of 0.50 mM. After an additional 96 hours incubation, the biosynthesis was terminated with the addition of two volumes of methanol and the broths clarified.

II. HPLC ANALYSIS

HPLC analysis was performed using a ES Industries Chromegabond FD column (5 um particle size; 4.6 mm ID by 25 cm length) at room temperature. UV detection was at 215 nm. The solvent system consisted of a gradient from 30% to 60% MeCN in HPLC-grade water containing 0.1% phosphoric acid (v/v) over a thirty minute period; the 90% MeCN was held an additional 5 minutes before a return to the starting solvent. The chromatograms obtained from the control (no added fluorobenzoic acids) and the experimental broth extracts were overlaid on the same time scale to compare results and a new peak identified as a 3-fluorobenzoic analog of zaragozic acid A, was detected.

III. ISOLATION AND PURIFICATION

Twenty mL of whole broth was combined with twenty mL methanol. The crude extract was filtered to remove cells, diluted with forty mL of DI water and applied to a water equilibrated $C_{18}$ Speed cartridge. After washing with water, the cartridge was eluted with twenty mL methanol. The eluate was reduced to dryness, then dissolved in two mL of 70% MeOH/$H_2O$. One mL was injected onto a Chromegabond FD column (4.6 mm × 250 mm). The column was developed as above. Detection was at 215 nm. Peaks with an elution time at 24.8 and 29.1 minutes were collected. Each fraction was diluted with four volumes of DI water, then applied to water-equilibrated $C_{18}$ SPE columns. After washing with five volumes of DI water, the columns were dried with nitrogen, then eluted with methanol. The eluates at 29.1 minutes were evaporated to dryness to yield the 3-fluorophenyl Zaragozic Acid A analog.

$^1$H NMR (400 MHz) (CD$_3$OD) 7.27 (dt, 8.1, 8.1, 6.2, 1H), 7.03 (dt, 7.1, 1.1, 1H), 6.93 (ddd, 10.2, 2.5, 1.7, 1H), 6.87 (m, 1H).

EXAMPLE 3

Compound of Formula (I) wherein $R_1$ is 4-fluorophenyl and $Z^1$, $Z^2$ and $Z^3$ are each hydrogen This compound was prepared following the procedure of Example 2 except that an equivalent amount of 4-fluorobenzoic acid (Na-salt) was employed. The retention time of the 4-fluorophenyl zaragozic acid A was identical with that of the 3-fluorophenyl derivative (29.1 minutes).

EXAMPLE 4

Compound of Formula (I) wherein $R_1$ is 2-fluorophenyl and $Z^1$, $Z^2$ and $Z^3$ are each hydrogen This compound was prepared following the procedure of Example 2 except that an equivalent amount of 2-fluorobenzoic acid (Na-salt) was employed. The retention time of the 2-fluorophenyl zaragozic acid A was 25.3 minutes.

$^1$H NMR (400 MHz) (CD$_3$OD) 7.28 (td, 7.6, 7.6, 1.7, 1H), 7.17 (m, 1H), 7.09 (td, 7.5, 7.5, 1.2, 1H), 6.99 (ddd, 10.3, 8.2, 1.3, 1H).

EXAMPLE 5

Compound of Formula (I) wherein $R_1$ is 2-furyl and $Z^1$, $Z^2$ and $Z^3$ are each hydrogen

I. DIRECTED BIOSYNTHESIS;

Culture MF 5453 was grown for 72 hours at 25° C. in KF medium and the cells harvested by centrifugation. The cells were washed twice with distilled water and resuspended to the original broth volume in 20 mM PIPES buffer (pH 6.1) containing 3% sucrose. Five mL aliquots of this suspension were transferred to 50 mL Erlenmeyer flasks and these flasks incubated at 25° C. with agitation. After 24 hours' incubation, 2-furoic acid (Na-salt) was added to a final concentration of 0.25, 0.5 and 1.0 mM. After an additional 96 hours incubation, the biosynthesis was terminated with the addition of two volumes of methanol and the broths clarified.

II. HPLC ANALYSIS

HPLC analysis was performed using a Beckman Ultrasphere ODS column at room temperature (5 um particle size; 4.6 mm ID by 25 cm length). UV detection was at 215 nm. The solvent system consisted of a gradient from 30% to 60% MeCN (plus HPLC-grade water containing 0.1% phosphoric acid by volume) over a thirty minute period; the 90% MeCN was held an additional 5 minutes before a 9 minute return to the starting solvent. The chromatograms obtained from the control (no added 2-furoic acids) and the experimental broth extracts were overlaid on the same time scale to compare results and a new peak identified as the 2-furyl analog of zaragozic acid A, was detected.

III. ISOLATION AND PURIFICATION

Six hundred thirty mL of whole broth was combined with an equal volume of methanol. The crude extract was filtered to remove cells, diluted with 1.5 L of DI water and applied to a 15 mm × 300 mm column packed with HP-20 (Mitsubishi Chemical, 220 mm bed height water equilibrated). After washing with water, the column was eluted with 200 mL methanol. The eluate was reduced to dryness, then dissolved in twenty mL of 60% MeOH in water. One mL was injected onto a Beckman Ultrasphere ODS column (10 mm × 250 mm). The column was developed at 3.0 mL/min using a gradient from 40% to 75% MeCN in HPLC-grade water containing 0.1% phosphoric acid (v/v) over a thirty minute period. Detection was at 215 nm. A peak eluting at 25.2 minutes was collected. The peak fraction was diluted with an equal volume of DI water, then applied to water equilibrated $C_{18}$ SPE column. After washing with DI water, the column was dried with nitrogen, then eluted with methanol. The eluate was evaporated to dryness to yield the titled compound.

$^1$H NMR (400 MHz) (CD$_3$OD) 7.34 (dd, 2.1, 0.9, 1H), 6.26 (dd, 3.1, 1.9, 1H), 6.05 (d, 3.0, 1H).

EXAMPLE 6

Compound of Formula (I) wherein R$_1$ is 2-thiophene and Z$^1$, Z$^2$ and Z$^3$ are each hydrogen

I. DIRECTED BIOSYNTHESIS:

Culture (MF-5453) was grown for 72 hours at 25° C. in KF medium and the cells harvested by centrifugation. The cells were washed (X2) with distilled water and resuspended to the original broth volume in 20 mM PIPES buffer (pH 6.1) containing 3% sucrose. Five mL aliquots of this suspension were transferred to 50 mL Erlenmeyer flasks and these flasks incubated at 25° C. with agitation. After 24 hours' incubation, thiophene-2-carboxylic acid (Na-salt) was added to a final concentration of 0.25, 0.5 and 1.0 mM. After an additional 96 hours incubation, the biosynthesis was terminated with the addition of two volumes of methanol and the broths clarified.

II. HPLC Analysis

HPLC analysis was performed using a Beckman Ultrasphere ODS column at room temperature (5 um particle size; 4.6 mm ID by 25 cm length). UV detection was at 215 nm. The solvent system consisted of a gradient from 30% to 90% MeCN (plus HPLC-grade water containing 0.1% phosphoric acid by volume) over a thirty minute period; the 90% MeCN was held an additional 5 minutes before a 9 minute return to the starting solvent. The chromatograms obtained from the control (no added thiophene-2-carboxylic acid) and the experimental broth extracts were overlaid on the same time scale to compare results and a new peak identified as the 2-thiophene analog of zaragozic acid A, was detected.

III. ISOLATION AND PURIFICATION

Two hundred mL of whole broth was combined with an equal volume of methanol. The crude extract was filtered to remove cells, diluted with 400 mL of DI water and applied to a 15 mm×300 mm column packed with HP-20 (Mitsubishi Chemical, 220 mm bed height water equilibrated). After washing with water, the column was eluted with 200 mL methanol. The eluate was reduced to dryness, then dissolved in twenty mL of 60% MeOH in water. Two mL injections were made onto a Beckman preparative HPLC (9.6 mm×250 mm) ODS column. The column was developed at 3.0 mL/min using a 35 minute linear gradient of 40% to 80% acetonitrile in water containing 0.1% H$_3$PO$_4$. Detection was at 215 nm. Peaks with an elution time at 28.9 and 30.4 minutes were collected and pooled. The pooled materials were diluted with four volumes of DI water then each applied to water-equilibrated C$_{18}$ SPE columns. After washing with five volumes of DI water, the columns were dried with nitrogen, then eluted with methanol. The eluate was evaporated to dryness to yield the titled compound.

$^1$H NMR (400 MHz) CD$_3$OD) 7.15 (dd, 5.0, 1.2, 1H), 6.90 (dd, 5.1, 3.4, 1H), 6.83 (dQ, 3.5, 1.0, 1H).

EXAMPLE 7

Preparation of an Ammonium Salt

A 0.1 mmol sample of the free acid of a compound of formula (I) is dissolved in 10 mL ethyl acetate. The resulting solution is saturated with gaseous ammonia and the ammonium salt precipitates from solution.

EXAMPLE 8

Preparation of a Potassium Salt

A solution of 0.1 mmol of the free acid of a compound of formula (I) in 10 mL methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added.

In a similar fashion, the sodium and lithium salts can be formed.

EXAMPLE 9

Preparation of a Calcium Salt

A solution of 0.1 mmol of the free acid of a compound of formula (I) in 20 mL 6:4 methanol:water is treated with an aqueous solution of 0.1 mmol of calcium hydroxide. The solvents are evaporated to give the corresponding calcium salt.

EXAMPLE 10

Preparation of an Ethylenediamine Salt

A solution of 0.1 mmol of the free acid of a compound of formula (I) in 10 mL of methanol is treated with 0.1 mmol of ethylenediamine. Evaporation of the solvent affords the ethylenediamine salt.

The procedure can also be applied to the preparation of the N,N"-dibenzylethylenediamine salt.

EXAMPLE 11

Preparation of a Tris(hydroxymethyl)aminomethane Salt

To a solution of 0.1 mmol of the free acid of a compound of formula (I) in 10 mL of methanol is added from 0.1 to 0.3 mmol of tris(hydroxymethyl)aminomethane dissolved in 10 ml of methanol. Evaporation of the solvent gives a corresponding salt form, the exact composition of which is determined by the molar ratio of amine added. Similarly prepared are the salts of L-ornithine, L-lysine, and N-methylglutamine.

EXAMPLE 12

Preparation of an L-arginine Salt

A solution of 0.1 mmol of the free acid of a compound of formula (I) in 20 ml of 6:4 methanol:water is treated with an aqueous solution of 0.1 to 0.3 mmol of L-arginine. Evaporation of the solvent affords the title salt, the exact composition of which is determined by the molar ratio of amino acid to the free acid of formula (I) used. Similarly prepared are the salts of L-ornithine, L-lysine and N-methylglutamine.

EXAMPLE 13

Preparation of a the trimethyl ester of a Compound of Formula (I) (Method I)

To 5 mg of the free acid of a compound of formula (I) in methanol (5 mL) is added 2 mL of freshly distilled diazomethane in ether (2.05M). After 5 minutes the solvent is removed to afford trimethyl ester as an oil.

EXAMPLE 14

Preparation of a the trimethyl ester of a Compound of Formula (I) (Method II)

To 0.6 mg of the free acid of a compound of formula (I) in 1 mL diethyl ether at 0 C. is added ethereal cyanamide dropwise until the solution remains yellow. The solution is evaporated under a stream of nitrogen to yield the trimethyl ester.

EXAMPLE 15

Preparation of a the tribenzyl ester of a Compound of Formula (I)

To a solution of 5 mg of the free acid of a compound of formula (I) in 0.5 mL tetrahydrofuran (THF) is treated at room temperature with 3 equivalents of N,N'-diisopropyl-O-benzyl isourea for 18 hours. The reaction mixture is then chilled to −15 C., and filtered to remove the urea. The filtrate is concentrated under reduced pressure to yield the tribenzyl ester.

The method of Example 15 is also suitable for the preparation of other ester derivatives such as 1) ethyl and the other lower alkyls, and 2) substituted benzyl esters, using the appropriately substituted isourea. By varying the number of equivalents of the substituted isourea used, the mono-, di-, and tri-substituted esters may be selectively prepared.

EXAMPLE 16

Oral Composition

As a specific embodiment of an oral composition of a compound of this invention, 20 mg of the compound from Example 1 is formulated with sufficient finely divided lactose to provide a total amount of 580 to 590 mg to fill a size 0 hard gelatin capsule.

What is claimed is:

1. A compound of structural formula (I)

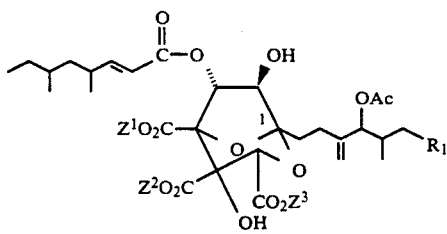

wherein $R_1$ is selected from the group consisting of:

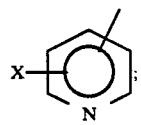

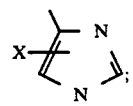

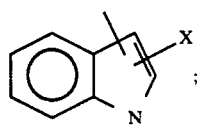

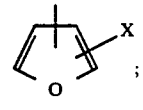

and

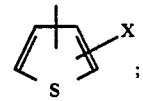

wherein X is selected from the group consisting of:
(a) H;
(b) halogen (F, Cl, Br, I);
(c) OH; and
(d) $CH_3$;

and wherein $Z_1$, $Z_2$ and $Z_3$ are each independently selected from the group consisting of:
(a) H;
(b) $C_{1-5}$alkyl;
(c) $C_{1-5}$alkyl substituted with a substituent selected from the group consisting of
  (i) phenyl, and
  (ii) phenyl substituted with methyl, methoxy, halogen (Cl, Br, I, F) or hydroxy; and
(d) a pharmaceutically acceptable cation.

2. The compound of claim 1 wherein $Z^1$, $Z^2$ and $Z^3$ are each independently selected from the group consisting of
(a) H,
(b) $C_{1-5}$alkyl;
(c) $C_{1-5}$alkyl substituted with phenyl;
(d) sodium, potassium, aluminum, calcium, lithium, magnesium or zinc;
(e) ammonia, N,N'-dibenzylethylenediamine, diethanolamine, N-benzylphenylethylamine, or diethylamine,
(f) N-methyl-glutamine, lysine, arginine; or ornithine;
(g) choline;
(h) chloroprocaine or procaine;
(i) piperazine;
(j) tetramethylammonium hydroxide; and
(k) tris(hydroxymethyl)aminomethane.

3. The compound of claim 2 wherein $R_1$ is selected from the group consisting of:

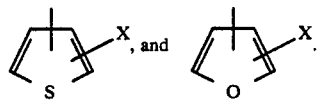

4. The compound of claim 3 wherein X is selected from the group consisting of H and F.

5. The compound of claim 4 wherein $Z^1$, $Z^2$, and $Z^3$ are each independently selected from the group consisting of:
(a) H,
(b) methyl,
(c) ammonium,
(d) potassium,
(e) sodium,
(f) lithium,
(g) calcium,
(h) ethylene diamine, (i) tris(hydroxymethyl)aminomethane,
(j) N,N'-dibenzylethylenediamine, and
(k) L-arginine.

6. The compound of claim 5 wherein $Z^1$, $Z^2$ and $Z^3$ are each hydrogen.

7. The compound of claim 6 wherein $R_1$ is selected from the group consisting of:
   (a) 3-thiophene;
   (b) 2-furyl; and
   (c) 2-thiophene.

8. A pharmaceutical composition comprising a nontoxic therapeutically effective amount of a compound of claim 1 and a pharmaceutically acceptable carrier.

9. A pharmaceutical composition comprising a nontoxic therapeutically effective amount of a compound of claim 1 in combination with a pharmaceutically acceptable non-toxic cationic polymer capable of binding bile acids in a non-resorbable form in the gastrointestinal tract and a pharmaceutically acceptable carrier.

10. A pharmaceutical composition comprising a nontoxic therapeutically effective amount of a compound of claim 1 in combination with a nontoxic therapeutically effective amount of a cholesterol lowering agent selected from the group consisting of:
    a) HMG-CoA reductase inhibitor;
    b) HMG-CoA synthase inhibitor;
    c) squalene epoxidase inhibitor;
    d) probucol;
    e) niacin;
    f) gemfibrozil;
    g) clofibrate; and
    h) LDL-receptor gene inducer.

11. A pharmaceutical composition comprising a unit dose of a compound of claim 1 and a nontoxic therapeutically effective amount of an HMG-CoA reductase inhibitor.

12. A method of treating hypercholesterolemia comprising the administration to a subject in need of such treatment a nontoxic therapeutically effective amount of a compound of claim 1.

13. A method of inhibiting squalene synthetase comprising the administration to a subject in need of such treatment a nontoxic therapeutically effective amount of a compound of claim 1.

14. A method for inhibiting fungal growth comprising applying to the area where growth is to be controlled an antifungally effective amount of a compound of claim 1.

15. A method of treating hypercholesterolemia comprising the administration to a subject in need of such treatment 20 to 100 mg of a compound of claim 1.

16. A method of inhibiting squalene synthetase comprising the administration to a subject in need of such treatment 20 to 100 mg of a compound of claim 1.

17. A method for inhibiting fungal growth in a living organism in need of such treatment comprising the oral, systemic or parenteral administration of a non-toxic antifungally effective amount of a compound of claim 1.

* * * * *